United States Patent [19] [11] 4,090,791
Siddiqi et al. [45] May 23, 1978

[54] DEVICE FOR CYCLICALLY REPEATING A SERIES OF COLORIMETRIC ANALYSIS ON EACH OF A SUCCESSION OF SAMPLES

[75] Inventors: Iqbal Siddiqi, Veyrier; Tito Suvā, Chatelaine, both of Switzerland; Christian Roehrich, Chaillevette, France

[73] Assignee: Battelle Memorial Institute, Carouge, Switzerland

[21] Appl. No.: 733,719

[22] Filed: Oct. 18, 1976

[30] Foreign Application Priority Data

Oct. 29, 1975 Switzerland ............... 13984/75

[51] Int. Cl.² .............................. G01J 3/50
[52] U.S. Cl. .................... 356/184; 23/253 R; 356/188; 356/244
[58] Field of Search ............ 23/253 R, 259; 356/180, 356/184, 186, 188, 201, 244, 246

[56] References Cited

U.S. PATENT DOCUMENTS 3,748,044 7/1973 Liston .................... 356/180
4,004,150 1/1977 Natelson .................. 356/246 X Primary Examiner—F. L. Evans
Attorney, Agent, or Firm—Karl F. Ross

[57] ABSTRACT

A device for colorimetric analysis of samples comprises a plurality of groups of receptacles, means for bringing these groups successively to a testing station, and means for automatically performing a cycle of analysis on the receptacles of the group at that station. The analysis means includes a light source, a photodetector aligned therewith, and a plurality of filters. The receptacles of each group and respective filters are moved successively into alignment with the source and detector so that the contents of each receptacle are analyzed with the aid of the correct corresponding filter.

10 Claims, 6 Drawing Figures

DEVICE FOR CYCLICALLY REPEATING A SERIES OF COLORIMETRIC ANALYSIS ON EACH OF A SUCCESSION OF SAMPLES

FIELD OF THE INVENTION

Our present invention relates to a device for colorimetrically analyzing a succession of samples in a recurrent cycle.

BACKGROUND OF THE INVENTION

Medicine makes ever-increasing use of the systematic analysis of organic liquids, in particular in the field of preventive medicine and in hospitals. Certain of these analyses are of colorimetric nature, carried out with the aid of a reagent designed to give the liquid a certain coloration, and a light source of a specified wavelength. This wavelength is obtained in practice by using a filter placed between the actual light source and the liquid sample. Often, the same sample has to undergo several analyses. To this end, the sample is divided between several test tubes each containing a specific reagent, a light beam of a predetermined wavelength is directed through each test tube, and the beams emerging from said test tubes are measured by a photometer.

Automatic equipment already exists for successively feeding the substances to be analyzed to a colorimetric analysis station, but this equipment is able to carry out only one type of analysis at a time. Consequently, the samples have to be grouped for each type of analysis. In the case of a series of samples each of which is divided into fractions to be subjected to a cycle of colorimetric analysis, the fractions of these samples which have to undergo the same type of analysis are grouped so that the organic liquid originating from the same subject is divided among as many groups as there are analyses in the cycle. This practice gives rise to serious identification problems, and constitutes a considerable source of error which is completely unacceptable in view of its gravity.

OBJECT OF THE INVENTION

The object of the present invention is at least partly to remedy the disadvantages of the aforementioned automatic equipment.

SUMMARY OF THE INVENTION

We realize this object, in accordance with our present invention, by means of a colorimetric analyzer comprising an intermittently rotated carrier provided with an annular array of separate, preferably discardable holders each including a respective set of transparent receptacles, these holders passing successively through a testing station equipped with a light source training a polychromatic beam upon a photometric detector. Several color filters are mounted on a common support located at the testing station and rotatable about an axis offset from that of the carrier. The receptacles of a given holder, on passing through the testing station, are successively interposed in the path of the light beam together with respective filters on the support which is intermittently rotated at a rate synchronized with the movement of the receptacles.

The receptacle holders may be independently rotatable on their carrier, about the axis of the filter support and jointly with the latter, upon arrival at the testing station. Alternatively, they may be complementary ring segments fixedly positioned on the carrier with their receptacles disposed along an arc centered on the carrier axis, each step of the carrier being then accompanied by a corresponding fractional rotation of the filter support. In either case, the receptacles of a set contain samples of the same specimen — generally a liquid — which is therefore individually associated with a given holder so as to eliminate an important source of possible error inherent in prior-art devices.

BRIEF DESCRIPTION OF THE DRAWING

The above and other features of our invention will now be described in detail with reference to the accompanying drawing in which.

SPECIFIC DESCRIPTION

Figure 1:
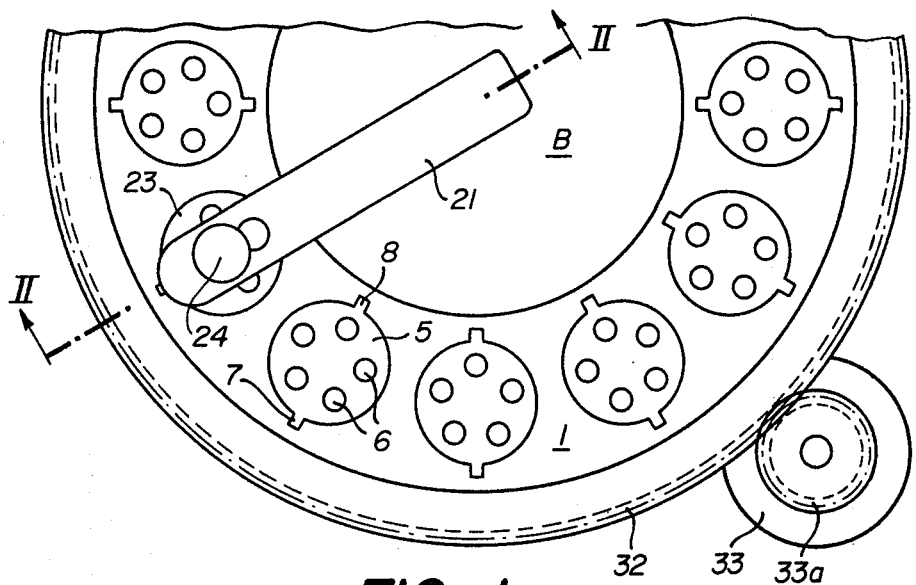
FIG. 1 is a plan view of part of a device representing an embodiment of our invention.
Figure 2:
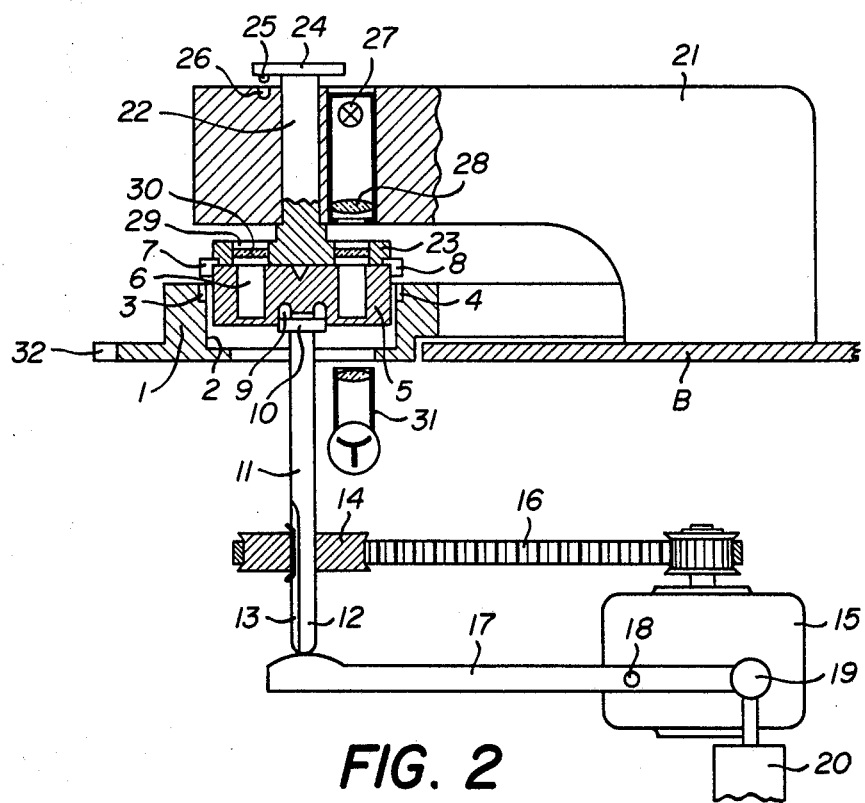
FIG. 2 is a section taken on the line II—II of FIG. 1.

The device shown in FIGS. 1 and 2 comprises a turntable 1 with a series of cylindrical seats 2 each provided with two positioning or indexing notches 3 and 4. Each seat receives a cylinder 5 provided with five cups 6 distributed at equal angular distances about the rotational axis of the cylinder. This cylinder is constructed of a transparent material such as a light-transmissive plastic, and comprises two positioning lugs 7 and 8 designed to engage in the notches 3 and 4, respectively. The lower face of the cylinder 5 contains a recess 9 complementary to the upper end 10 of a drive spindle 11. The other end 12 of the spindle has a slot 13 for keying thereon a pinion 14 connected to a stepping motor 15 by a toothed belt 16. The lower end 12 of spindle 11 rests on the end of a lever 17 pivoted about a fixed axis 18 and articulated to the armature 19 of an electromagnet 20.

An arm 21 rigid with the frame B of the device extends above the turntable 1 at a testing station shown in FIG. 2. The end of arm 21 carries a disc 23 rigid with a vertical rod 22 which passes through the arm 21 and terminates in a small plate 24 provided with a positioning pin 25 designed to engage in a blind hole 26 provided on the upper face of the arm 21.

The arm 21 also carries a light source comprising a bulb 27 and a lens 28 designed to form a light beam. The disc 23 is traversed by five circular passages 29 distributed at equal angular distances about its rotational axis. This disc also has two peripheral notches designed to fit over the lugs 7 and 8 of the cylinder 5. These notches are designed so that when they are fitted over the lugs each of the five passages 29 will register with a respective cup 6 of the cylinder 5. Each passage 29 contains a filter 30 designed to pass only one predetermined wavelength of the beam emitted by the bulb 27. This wavelength is chosen in accordance with the colorimetric analysis which is to be carried out.

A photometer 31 fast with the frame B is located below the turntable 1 and is aligned with the axis of the beam emitted by the light source 27, 28. The outer peripheral edge of the turntable 1 carries toothing 32 engaged with a pinion 33a driven by a stepping motor 33.

Figure 3:
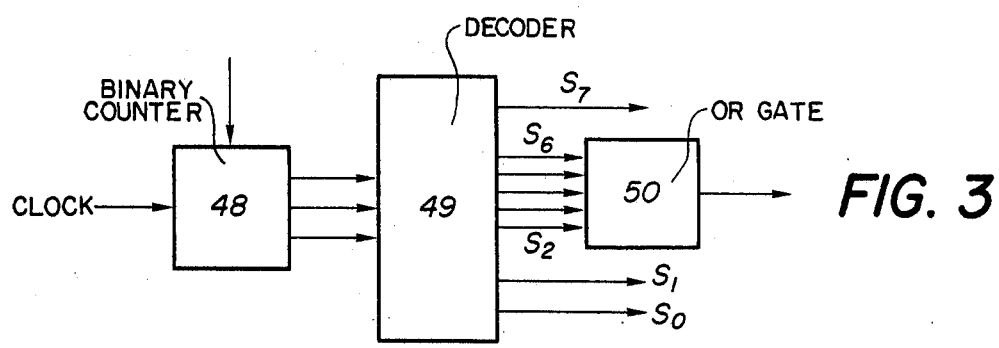
FIG. 3 is a block diagram of a control circuit for the device shown in FIGS. 1 and 2.

The described device is controlled by a timing circuit shown in the block diagram of FIG. 3, which comprises a binary counter 48 supplied with clock signals and connected to a decoder 49 by way of three outputs. This decoder comprises eight outputs $S_0$ to $S_7$. The output $S_0$ is connected to the stepping motor 33. The outputs $S_1$ and $S_7$ are connected to the electromagnet 20 and serve for respectively energizing and de-energizing same. Finally, the outputs $S_2$ to $S_6$ are connected to an OR gate 50 for controlling the stepping motor 15. The decoder 49 successively energizes the outputs $S_0$ to $S_7$ under the control of the binary counter 48, in a recurrent cycle. Consequently, the motor 33 receives the first pulse of the cycle, then the electromagnet 20 is activated, then the five subsequent pulses operate the motor 15, followed by de-energization of the electromagnet 20. The operations carried out at each stage of the cycle are described hereinafter.

Only the components necessary for understanding the invention have been shown and described. The disclosed device normally forms part of automatic analysis equipment comprising a pipette for transferring samples of organic liquid from test tubes to the cups 6 of the cylinders 5, and also a station for replacing the used cylinders with fresh ones. Transferring and filling stations are well known in this type of equipment. Moreover, the equipment described may or may not comprise such or other components, without influencing the analysis process hereinafter described.

It will be assumed that all the cups 6 of the cylinders 5 are filled with a solution containing urine and a reagent, which may be different for each cup of any one cylinder 5, the cups occupying corresponding angular positions in each cylinder receiving the same reagent, this angular position being defined in relation to the radius of the turntable 1 passing through the center of each cylinder 5. Consequently each cylinder 5 arrives under the arm 21 in the same angular position.

When a cylinder 5 arrives under the arm 21, the armature 19 of the electromagnet is attracted downwards so that the lever 17 pivots about its fulcrum 18 and causes the spindle 11 to rise, its upper end 10 engaging in the recess 9 and pushing the cylinder 5 against the disc 23 carrying the filters 30. The cylinder 5 is disengaged from its seat 2 at the same time as the positioning lugs 7 and 8 become disengaged from the notches 3 and 4. These lugs, which project beyond the upper face of the cylinder, now couple that cylinder with the disc 23 by centering corresponding peripheral notches in the disc, pushing the latter upwards and disengaging the pin 25 of the plate 24 from the bore 26, as shown in FIG. 2.

At this moment, the cylinder facilitates the colorimetric measurement of the solution contained in the first cup. Once this measurement has been made, the motor 15 drives the cylinder 5, by means of the toothed belt 16, through exactly one fifth of a revolution to bring the next cup into line with the axis of the beam emitted by the light source 27, 28. This rotation is transmitted to the cylinder 5 by the drive spindle 11 and is also transmitted by the cylinder 5 to the disc 23 by way of the positioning and coupling lugs 7 and 8. Consequently, each filter 30 is associated with one specific cup 6 and follows the angular movement of that cup. When the contents of all the cups have been analyzed, the disc 23 will have made one complete revolution so that it has returned to the same position which it occupied at the moment when the cylinder 5 arrived under the arm 21.

When the contents of the five cups 6 of the cylinder have been analyzed, the lever 17 is lowered and the spindle 11 becomes disengaged from the cylinder 5. The drive motor 33 for the turntable 1 advances through one step to bring the following cylinder 5 under the arm 21, and the same analysis process is repeated for this cylinder.

Figure 4:
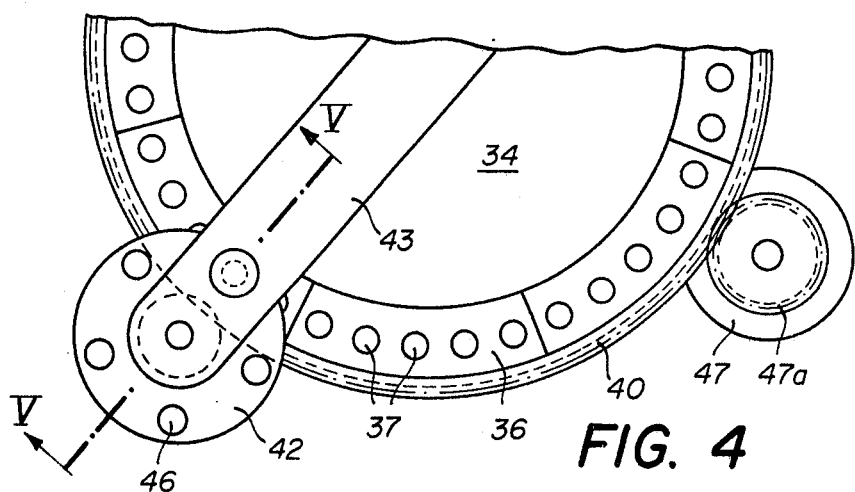
FIG. 4 is a plan view similar to FIG. 1, representing another embodiment.

The embodiment shown in FIG. 4 comprises a disc 34 having an annular rabbet 35 designed to receive blocks 36 in the form of ring sectors, in which the analysis cups 37 are provided. Each of these blocks 36 has a bore engageable by a positioning lug 38 which projects from the disc into the notch 35. The outer peripheral edge of the disc 34 has teeth 40 meshing with a pinion 41 which is fixed concentrically to a disc 42, carrying filters 46, and is rotatably mounted under an arm 43 rigid with the frame of the device. A light source 44 is mounted on the arm 43 and a photodetector 45 is disposed, in line with the axis of the light beam emitted by the source 44, below the disc 34. The path described by the filters 46 in the disc 42 intersects the axis of the light beam, which traverses the circular path of the cups 37.

The ratios between the pitch-circle diameters of the toothing of disc 34 and pinion 41 as well as between the angular separations of the cups 37 and of the filters 46 are so chosen that the passage of two successive cups 37 into line with the axis of the light beam coincides with the passage of two successive filters 46 into line with the axis of the light beam. The disc 34 is driven by a pinion 47a of a stepping motor 47, meshing with the toothing 40.

In the example illustrated, each block 36 comprises five cups 37 and the disc 42 comprises five filters 46, so that the analysis cycle comprises five analyses, the cycle being repeated for each block 36. Each of the five cups 37 of any one block 36 is designed to receive a dose of urine from the same person, the five cups containing the respective reagents designed for specific analysis of the urine.

In either of the described embodiments, the various analyses to be carried out on samples withdrawn from the same person are grouped into a cycle which is repeated for successive groups of samples. The number of analyses in the cycle can of course be other than five, this figure having been chosen only as an example. The problems of identifying the samples with the person to whom they belong are considerably simplified, especially if the various samples from this person are distributed in the cups provided on one and the same support 5 or 36. In this case only the support needs to be identified, as all the samples which it contains must come from the same person. The means for feeding the samples and reagents, and the positioning of the cylinders 5 or blocks 36, have not been shown as they do not form part of the invention. Preferably the cylinders 5 or blocks 36 serve for only a single cycle of analysis and are then thrown away. The transfer of the samples into the cups is preferably carried out on the device itself. The device could comprise mixing and incubation means which also have not been shown since they are not pertinent to the invention.

Figure 6:
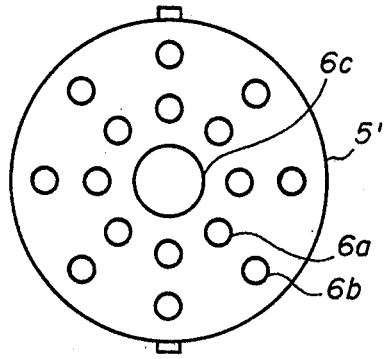
FIG. 6 is an enlarged plan view of a modified receptacle carrier for the embodiment of FIGS. 1 and 2.
Figure 5:
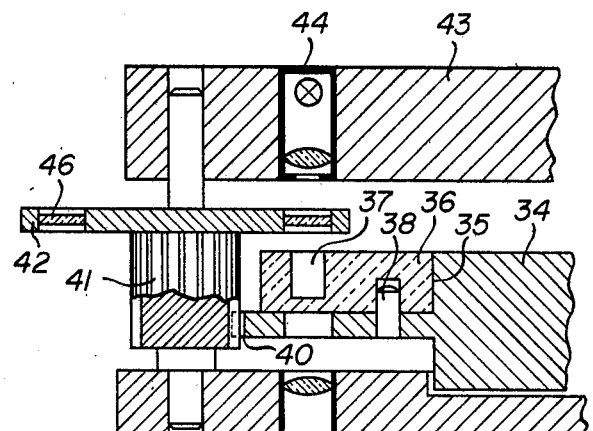
FIG. 5 is a section taken on the line V—V of FIG. 4.

FIG. 6 shows a modification of the cylinders illustrated in FIGS. 1 and 2, designed for bichromatic analysis. Each modified cylinder 5' comprises eight pairs of cups 6a, 6b, the cups of each pair being aligned along a respective radial direction of the cylinder 5' and the pairs of cups being angularly equispaced on the cylinder. The center of the cylinder 5' may be occupied by a cup 6c of greater volume than the other cups, designed to receive the sample to be distributed into the cups 6b. The rest of the apparatus is similar to that shown in FIGS. 1 and 2, the apparatus being simply adapted to carry out two series of eight analyses per cylinder instead of five. To this end, a second light source and a second photometer are provided to analyze the substance contained in the second cup of each pair. Furthermore, the disc 23 is provided with two concentric sets of filters, grouped in pairs in the manner of the cups 6a and 6b of the cylinder 5', the wavelengths of the filters of each pair being either identical or different.

In practice, the second cup serves to establish a reference for comparison with the value measured for the sample. Consequently, one cup of each pair, for example the cup 6a, receives the sample to be analyzed mixed with an appropriate reagent, while the cup 6b receives the reagent alone. The photometer measuring the light leaving the cup 6b enables a reference to be established for comparison with the light leaving the cup 6a and measured by the other photometer.

We claim:

1. A device for carrying out a series of colorimetric analyses on respective sets of samples in a recurrent cycle, comprising:
    a carrier rotatable about a first axis;
    a multiplicity of separate receptacle holders mounted on said carrier in an annular array centered on said first axis, each of said holders including a plurality of transparent receptacles forming a set adapted to contain samples taken from a common specimen;
    a testing station provided with a light source emitting a polychromatic beam and a photometric detector in the path of said beam;
    drive means for successively moving said holders through said testing station by intermittently rotating said carrier, with consecutive stepping of all receptacles of a set across the path of said beam;
    a support at said testing station rotatable about a second axis offset from said first axis; and
    a plurality of color filters peripherally equispaced on said support for consecutive interposition in the path of said beam, said drive means including transmission means for intermittently rotating said support about said second axis in synchronism with the stepping of said receptacles for joint translumination of each filter and a respective receptacle temporarily aligned therewith, all the receptacles of a set being transluminated during a single rotation of said support.

2. A device as defined in claim 1 wherein said holders are independently rotatable on said carrier about individual axes aligned with said second axis upon arrival of each holder at said testing station, the receptacles on each holder being disposed on a circle centered on the holder axis with an angular pitch corresponding to that of said filters on said support whereby each filter registers with a respective receptacle upon alignment of the holder axis with said second axis, said support and said holders being provided with coacting coupling formations for rotary entrainment of an aligned holder by said support upon rotation of the latter by said transmission means.

3. A device as defined in claim 2 wherein said drive means comprises a first motor coupled with said carrier, a second motor coupled with said support by way of said transmission means, and control means for alternately stepping said first and second motors.

4. A device as defined in claim 3 wherein said control means comprises a timing circuit responsive to a train of clock signals.

5. A device as defined in claim 2 wherein said transmission means includes a mechanism for axially shifting an aligned holder into coupling engagement with said support, said carrier being provided with indexing formations maintaining each holder in a predetermined relative position prior to axial shifting thereof by said mechanism.

6. A device as defined in claim 1 wherein said holders are complementary ring segments fixedly positioned on said carrier, said receptacles being disposed on each holder along an arc centered on said first axis, said transmission means comprising a toothed linkage between said carrier and said support.

7. A device as defined in claim 6 wherein said carrier is a disc with peripheral gear teeth, said linkage including a pinion rigid with said support in mesh with said gear teeth.

8. A device as defined in claim 7 wherein said disc is provided with a peripheral rabbet, said ring segments being mounted on said rabbet.

9. A device as defined in claim 1 wherein said light source and said detector lie in a vertical line parallel to said axes.

10. A device as defined in claim 1 wherein said holders are individually detachable from said carrier for discarding after a single use.

* * * * *

Dedication 4,090,791.—*Iqbal Siddiqi*, Veyrier and *Tito Suva*, Chatelaine, Switzerland and *Christian Roehrich*, Chaillevette, France. DEVICE FOR CYCLICALLY REPEATING A SERIES OF COLORIMETRIC ANALYSIS ON EACH OF A SUCCESSION OF SAMPLES. Patent dated May 23, 1978. Dedication filed Mar. 26, 1984, by the assignee, *Battelle Memorial Institute*.

Hereby dedicates to the People of the United States the entire remaining term of said patent.

[*Official Gazette May 15, 1984.*]